United States Patent [19]

Relyveld et al.

[11] 4,350,686

[45] Sep. 21, 1982

[54] ALLERGEN COMPOSITION AND METHOD FOR PREPARATION THEREOF

[75] Inventors: Edgar R. Relyveld; Emile Henocq, both of Paris, France

[73] Assignee: Institut Pasteur, Paris, France

[21] Appl. No.: 194,577

[22] Filed: Oct. 6, 1980

[30] Foreign Application Priority Data

Oct. 8, 1979 [FR] France .................. 79 24948

[51] Int. Cl.$^3$ ............... A61K 39/00; A61K 39/36
[52] U.S. Cl. .................................. 424/88; 424/91
[58] Field of Search ............................. 424/88, 91

[56] References Cited

U.S. PATENT DOCUMENTS 4,123,427 10/1978 Daniel ............................. 424/88
4,163,778 8/1979 Ohman ........................... 424/91

FOREIGN PATENT DOCUMENTS 962592 2/1975 Canada.

OTHER PUBLICATIONS

Ohman et al.-Chem. Abst. vol. 79 (1973) pp. 144,754c
Stokes et al.-Chem. Abst. vol. 83 (1975) pp. 176, 503u.
King et al.-Biochemistry vol. 3, No. 3 (1964) pp. 458-468.
Underdown et al.-Biochemistry vol. 8 No. 3 (1969) pp. 980-989.
Palmsterna-Chem. Abst. vol. 56 (1962) p. 10764c.
King et al.-Chem. Abst. vol. 57 (1962) p. 10170a.
King et al.-Biochemistry vol. 1 No. 4 (1962) pp. 709-720.
Robbins et al.-Chem. Abst. vol. 60 (1964) p. 14989b.
Roebber et al.-J. Of Immunology vol. 115 No. 1 Jul. 1975 pp. 303-304.
Johnson et al.-Chem. Abst. vol. 63 (1965) 10487b.
Harris-Chem. Abst. vol. 84 (1976) 3173d.
Harris-Chem. Abst. vol. 78 (1973) p. 109129k.

*Primary Examiner*—Sam Rosen
*Attorney, Agent, or Firm*—Toren, McGeady & Stanger

[57] ABSTRACT

The invention involves a process of preparing purified stable allergens from various materials.

8 Claims, 2 Drawing Figures

ALLERGEN COMPOSITION AND METHOD FOR PREPARATION THEREOF

BACKGROUND OF THE INVENTION

1. Field of the Invention

The invention relates to the preparation of allergens, to which it imparts an improvement permitting the obtention of improved allergenic compositions; the latter also form part of the invention.

2. Description of the Prior Art

Allergology has assumed an important position in therapy in recent decades, and its role is expanding; not only does it detect the allergic character in various old diseases, but it is also called on to remedy attacks of this type which are multiplied by modern pollution. Likewise there is always a need for good hyposensitizing agents, in spite of the presence on the market of well-known allergens extracted from various materials, such as: pollens, flours, house dusts, hair, kapok, feathers, molds, etc. Although a number of preparations, particularly retard-allergens adsorbed on mineral supports such as gels with an alumina base, for example, yield excellent results, the inocuity and constancy of activity of some of them leave something to be desired. The duration of use of several allergenic extracts available at the present time, is therefore limited in time.

SUMMARY OF THE INVENTION

The present invention confers an improvement making it possible to obtain much more stable and more active allergens which provoke no secondary reactions in the organism in which they are injected. The improved allergens produced according to this invention have a considerably longer useful life and they lend themselves particularly well to the preparation of the form adsorbed on a mineral gel.

The invention results from the discovery of a phenomenon, heretofore unknown in this field; the presence of various enzymes in the allergenic extracts was not considered as unfavorable, and it was even proposed to profit by it in classifying or appreciating their activity (GLEIGH G.J et coll, "Allergy and Clinical Immunology"-Excerpts Medical, Amsterdam, 1977, pages 184 and 213); but the Institut Pasteur has found that at least some of these enzymes degraded constituent proteins of the allergens. Thus, unexpectedly, the Applicants have determined the cause of the instability of the allergenic extracts; they also found that the enzymes, responsible for the attack on the useful proteins, as well as other impurities, interfere with the adsorption of allergens on mineral adjuvants. In addition, these, or some of these enzymes can be the cause of the production of antibodies, by a reaction of the organism against the impurities which they constitute in the allergen injected.

The improved method, according to the invention, therefore comprises the elimination of the enzymes present, from the aqueous extract of an allergen, as soon as possible after the preparation of this extract. It is a question, as a matter of fact, of allowing the least possible time for the attack on the useful proteins by the proteases of the medium present.

Thus the process according to the invention, which comprises the preparation of an aqueous extract of allergen, is characterized by the elimination, from this extract, of substances not having the desired allergenic activity. In a particular form of execution, the solution is allowed to retain only the allergenically active substances whose molecular masses range from about 10,000 to 50,000, and particularly from 14,000 to 45,000 (by precipitation).

DESCRIPTION OF THE PREFERRED EMBODIMENT

Figure 1:
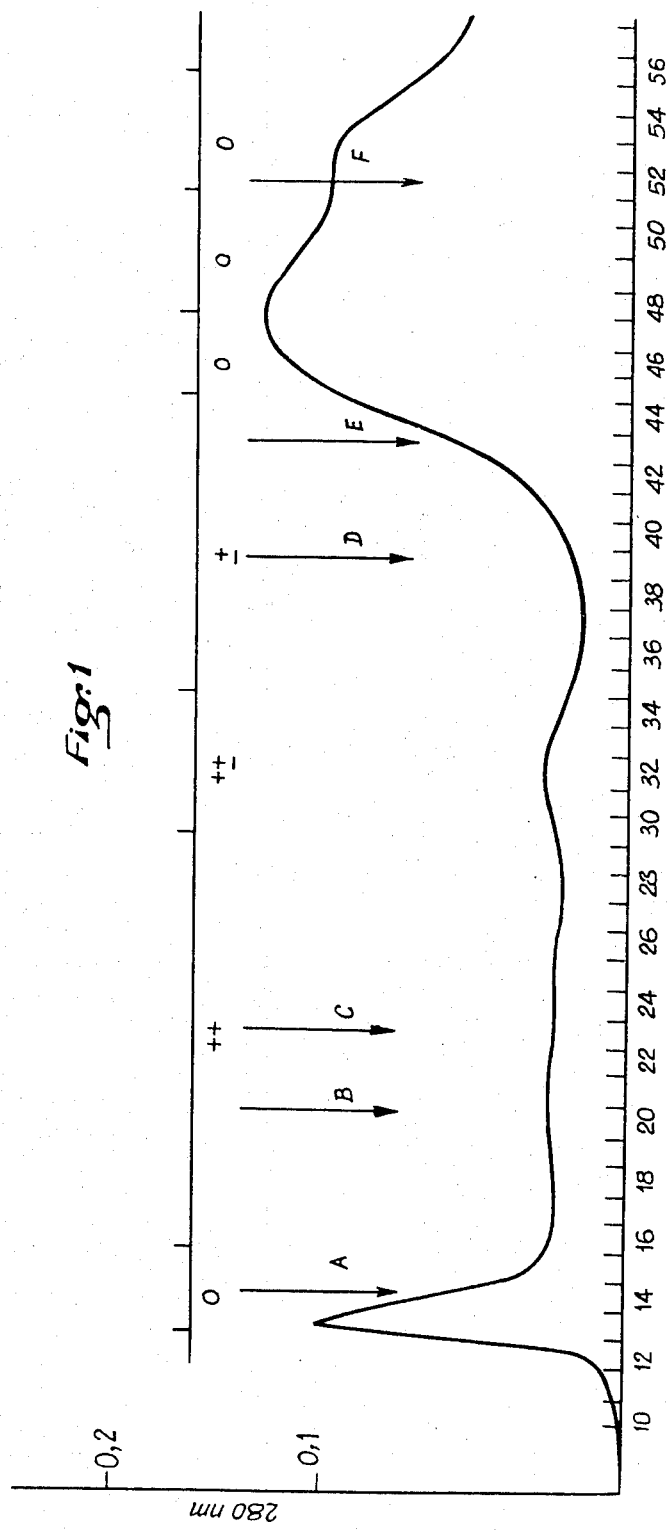

In the practice of the invention, it is, moreover, desirable to carry out the abovementioned operation on an extract already freed of various other impurities: this is done in known fashion, by the precipitation and redissolution of the proteins in the extract.

The elimination of the inactive fractions, particularly those whose molecular masses are below 10,000 or 14,000, and above 55,00 or 45,000, according to the invention, can be embodied by any appropriate means, well known in the art, for example, chromatographic methods, fractional precipitations, electrophoresis, etc. Filtration on gel, in this manner of working, renders valuable service, and there is a description below, by way of non-limiting example, of the fractioning of a pollen extract by molecular screening.

The methods of extraction of protein from various materials, in particular with a view to the preparation of allergenic compositions, are known, and there is no need to describe them here. By way of example, however, an operational method will be discussed, which is particularly siutable and which has been the subject of publications such as French Pat. No. 1,604,135. This method consists in treating 100 g of material, particularly pollens, with 1 liter of a solution of $Na_2HPO_4$. $12H_2O$ at 25 g/l, containing 1/10,000 of merthiolate. After 24 hours of agitation at +4degC, the solution is separated from the solid by centrifuging. The crude extract thus obtained is purified by saline precipitation, which consists in adding 604 g of crystallized ammonium sulfate to 1 liter of this extract, and leaving it in contact, with agitation, for 3 h at +4degC. The precipitate formed is then separated by centrifuging and redissolved in a solution of disodium phosphate at 25 g/l containing 1/10,000 of merthiolate. The solution obtained is dialyzed against a fresh solution of disodium phosphate at 25 g/l, again supplemented by merthiolate.

It is on an extract, that is to say a solution prepared as indicated above, from phleum pollen, that the operations brought to light in the remainder of the present description were carried out.

This solution is first subjected to a fractioning by molecular screening. To do so, a chromatographic column, 35 mm in diameter and 560 m high is used; it is charged with Sephadex G-100, whose range of possible fractioning extends over the molecular masses of 4,000 to 150,000. The fractioning is conducted with an eluent constituted by a solution of disodium phosphate at 25 g of $Na_2HPO_4$. $12H_2O$ per liter, containing 0.9% of NaCl 1/10,000 of merthiolate. The operation is conducted on 5 ml portions of extract, each of them being followed by a passage through the elution buffer. Fractions of 10 ml are collected, on which are determined:

The molecular mass of the dissolved substance,

The presence of enzymes, and

The reaction on the skin.

Furthermore, a similar fractioning, and the abovementioned determinations are made on an extract of phleum pollen in disodium phosphate, of the same concentration, but not yet purified by precipitation in ammonium sulphate: this solution is called crude extract in the remainder of the description.

The results of these tests are reported in the attached tables and graphs.

FIG. 1 shows the curve of elution of the crude extract of phleum pollen: the numbers of the fractions of 10 ml are plotted in the abscissa, while the ordinate indicates the absorbance at 280 nm. At the top of the graph, on a line parallel to the abscissa, are the reactions on the skin of the fractions mixed, from the 13th to the 55th fraction. Letters A to F designate the reference marks of substances with known molecular masses:

| A - Dextran blue | mol. mass. | 2,000,000 |
| B - Albumin | mol. mass. | 65,000 |
| C - Egg albumin | mol. mass. | 45,000 |
| D - Lysozyme | mol. mass. | 14,600 |
| E - Bacitracine | mol. mass. | 1,450 |
| F - DNP ethanolamine | mol. mass. | 227 |

The reaction on the skin is determined by the known "prick" method, which consists in placing a drop of liquid on the skin and pricking through this drop with a needle; after 20 minutes approximately, an allergic subject presents a positive reaction, noted +, that is to say a papule and an erythema. A single + signifies that the papule extends over an average diameter of 5 mm; the number of +'s indicates the multiples of 5 mm observed.

In the case of the curde extract in FIG. 1, a skin reaction is noted for the combined fractions no. 16 to 29 (++), 30 to 34 (+±) and 35 to 44 (+): there is no reaction before fraction 15 nor after fraction 45, which signifies that outside of fractions 16 to 44 there is no longer a product of any interest as an allergen. The useful range therefore ranges from no. 16 to no. 44.

Figure 2:
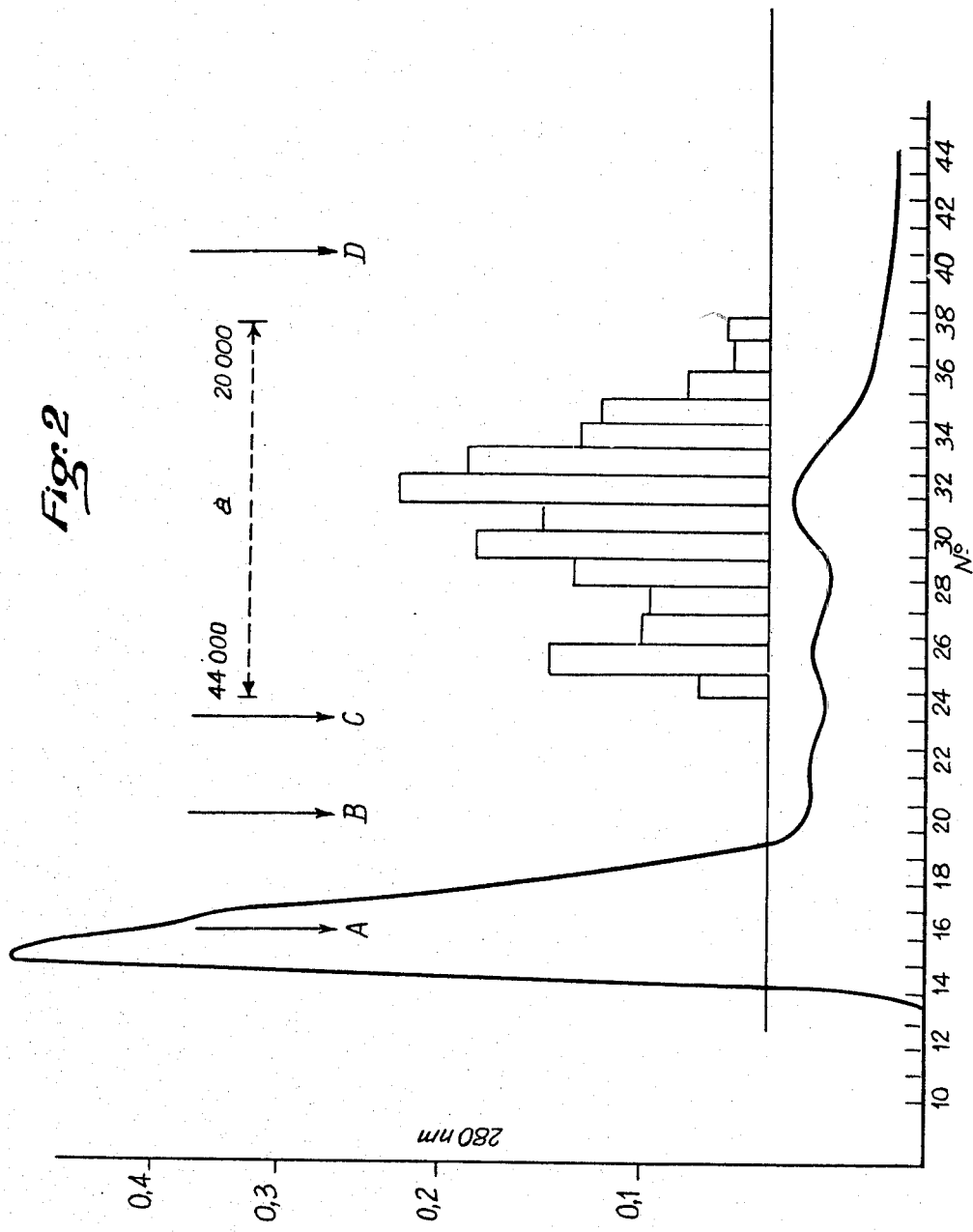

FIG. 2 shows the elution diagram, analogous to that in FIG. 1, but applied to the extract of phleum pollen previously purified by precipitation in ammonium sulfate and redissolution in a solution of disodium phosphate; it is therefore the proteins almost exclusively, which are thus subjected to the separation by molecular screening. On this graph, the series of vertical rectangles represents the only fractions of interest, yielding reactions of + to +++ on the skin of allergic subjects, determined by the prick method. The heights of the rectangles are proportional to the diameter of the papules formed on the skin: 25 mm of this height corresponds to 5 mm of papule diameter. The useful range comprises fractions no. 25 to 38, corresponding essentially to molecular masses of 44,000 to 20,000. Here again are the indications provided by the crude extract in FIG. 1, but with a contraction of the useful range.

According to the invention, in the present case, given by way of example, only fractions no. 25 to 38 are collected for preparation of the allergenic composition, while the other fractions are discarded, in contrast to previous practice.

The proof that the adopted fractions 25 to 38 contain practically no enzymes is provided by measurements made by the very practical method known as the "API ZYM" system. This method consists in introducing, into a series of 20 cupels, the bottom of which is constituted by a support containing the enzymatic substrate with its buffer, of a small amount of liquid to be studied, and, after incubation, in reacting this liquid with two reagents, tris (hydroxy-methyl)-amino-methane and rapid blue BB. The presence of enzymes manifests itself by the coloration appearing in the cupels, which is rated on a scale of 1 to 5, the latter figure corresponding to maximum intensity. With the aid of this system, certain authors have been able to find the presence of numerous enzymes in extracts of graminaceous pollen; thus, Jean Bousquet et col, made measurements (Annals of Allergy, vol. 41, September 1978, p. 164–169) concerning a whole series of enzymes such as phosphatases, esterases, lipases, leucine-amino-peptidase, valine-amino-peptidase, trypsin, chymotrypsin, beta-glucose-aminidase, glucosidases, etc.

By applying the API ZYM system to the products in FIG. 1 and 2, described above, the results given in table 1 below were found. This table presents, for the cupels in the API system, the rating (from 0 to 5) determined by comparison of the colored scale of the system with the shade developed in the cupel. The letters "tr" stand for "trace." The tests are, of course, accompanied by a control sample formed by a solution of disodium phosphate at 25 g/l containing merthiolate, and a heated extract of pollen.

The result of the data in table 1 is that the crude extract definitely contains enzymes and that the content thereof is somewhat diminished owing to the purification in ammonium sulphate. The enzymes disappear almost completely following the fractioning by filtration on gel; practically none remain beyond the 22nd fraction; but, there are some in fractions 14 to 18 which lack allergenic activity.

(See table 1)

It was mentioned above that the elimination of the components of molecular masses below 14,000 and above 45,000 also improve the adsorption of the allergen by mineral gels. Thus it can be noted that the useful fractions, separated according to FIG. 2, are adsorbed better on known adsorbents, such as for example, alumina, phosphate of alumina or phosphate of calcium. The adsorption is particularly effective for the special phosphate in which the ponderal ratio Ca/P is comprised between 1.55 and 1.90, as described in French Pat. No. 72,12036 (publication No. 2.181.426 of 12/7/73), preferably 1.65 to 1.85.

Such a gel is prepared, in particular, by mixing a solution of 25 g of disodium phosphate in 1 liter of water, with 2/10,000 of merthiolate supplemented by 20 ml of allergenic extract, prepared from 100 g of pollen, as indicated at the start of the present description. To the mixture obtained, 1 liter of water, containing 10.2 g of $CaCl_2 \cdot 2H_2O$ is added. This addition is made very rapidly under agitation, and the pH of the medium is brought to 6.8–7 by means of normal soda.

In a first series of tests, the prick method mentioned above was used to determine the reaction on the skin of 11 patients. For each of them, an extract of phleum, purified by precipitation in ammonium sulfate was used, plus—furthermore—the liquid supranatant after precipitation of the special calcium phosphate in the presence of the same extract, as just indicated. In both cases, the dilution of the extract is 1/1000. The results are again indicated by means of +'s, each of which corresponds to 5 mm of papule formed on the skin of the patient.

(See table 2).

It is clear that the adsorption was very effective, since the overall diminution of the reaction on the skin was $(22 - 8.5)/22 = 61.4\%$ Similar tests were run with the same special calcium phosphate, no longer mixed with the total phleum extract, but with the enzymeless fractions, represented and described in regard to FIG. 2. The reactions on the skin were determined at dilutions ranging from 1/1,000 to 1/1,000,000, table 3 shows the results thereof, compared on the one hand for the extract, that is to say the fractions themselves, and on the other hand, on the liquid supranatant after the precipitation of the phosphate. For the dilution of 1/1,000, the reaction is determined by the prick method, while the intradermal reaction is used for the other dilutions.

(See table 3).

It is seen that the adsorption of the fractioned phleum extract is very extensive.

Similar results are obtained with extracts obtained from other pollens, in particular those of rye, cockle, dactylis, etc.

Table 1 (see original text)

A. Sample B. Concentration C. Numbers of cupels
1. Control
2. Total crude extract (FIG. 1)
3. Total extract purified in $NH_4$ sulf. (FIG. 2)
4.4 Ditto, fractions 14 to 18 (etc.)

Table 2 (see original text)

A. Patient No.
1. Extract
2. Supranatant

Table 3 Dilutions (see original text)

A. Patient No. B. Liquid extract C. Supranatant

We claim:

1. A method for preparing a stable allergen aqueous composition which comprises the steps of:
   (a) extracting allergen from a material selected from the group consisting of pollen, flour, house dust, kapok, wool and molds to form an aqueous solution and separating the solution from the solid material;
   (b) precipitating the allergen from said aqueous solution and separating the precipitate;
   (c) redissolving the allergen in a disodium phosphate aqueous solution;
   (d) shortly after step (c), fractionating the solution with respect to the molecular masses of components dissolved therein and discarding the fractions which contain components having molecular masses lower than 10,000 and those have molecular masses higher than 55,000; and
   (e) recovering the fractions of said solution which contain components, the molecular masses of which are in the range of 10,000 to 55,000.

2. The method of claim 1 wherein the extraction of allergen from said material is carried out by stirring the material with an aqueous solution of disodium phosphate for several hours and then separating it from the solution.

3. The method of claim 1 wherein the precipitation of the allergen is effected by adding crystallized ammonium sulfate to the aqueous solution obtained by the extraction of allergen and the precipitate formed is separated from the solution.

4. The method of claim 1 wherein the solution of allergen obtained by redissolving the precipitated allergen in a disodium phosphate aqueous solution is dialyzed against a fresh solution of disodium phosphate.

5. The method of claim 1 wherein the fractionation is carried out by elution chromatography and the elution agent is an aqueous disodium phosphate solution.

6. The method of claim 1 which comprises the further step of admixing the recovered solution with an aqueous gel of alumina, aluminum phosphate, or calcium phosphate whereby allergen is adsorbed by the gel.

7. A method for preparing a stable allergen aqueous composition comprising:
   (a) extracting allergen from a material selected from the group consisting of pollen, flour, house dust, kapok, wool and molds by contacting the material with an aqueous solution of about 25 g disodium phosphate per liter for 24 hours, at a temperature of about 4° C. with stirring, and then separating the solution from the material;
   (b) adding about 604 g of ammonium sulfate crystals per liter of separated solution whereby allergen is precipitated and separating the precipitate formed from the solution;
   (c) redissolving the precipitate in an aqueous solution having about 25 g disodium phosphate per liter and an antiseptically effective amount of an antiseptic agent, and then dialyzing the solution thus obtained against a disodium phosphate aqueous solution having 25 g of phosphate per liter;
   (d) shortly after step (c), fractionating the last solution obtained by molecular screening with respect to the molecular masses of the components it contains, while discarding the fractions having components of molecular masses below 14,000 and above 45,000; and
   (e) recovering the fractions which contain components whose molecular masses are in the range of 14,000 to 45,000.

8. The method of claim 7 which comprises the further step of admixing the recovered solution with an aqueous gel of calcium phosphate in which the weight ratio Ca/P is 1.62 to 1.85 whereby allergen is absorbed by the gel.

* * * * *

UNITED STATES PATENT AND TRADEMARK OFFICE
CERTIFICATE OF CORRECTION

PATENT NO. : 4,350,686

DATED : September 21, 1982

INVENTOR(S) : Edgar H. Relyveld et al.

It is certified that error appears in the above-identified patent and that said Letters Patent is hereby corrected as shown below:

On the title page Item /75/ Inventors:

"Edgar R. Relyveld; Emile Henocq, both of Paris, France:" should read -- Edgar H. Relyveld; Emile Henocq, both of Paris, France --.

Signed and Sealed this

Twenty-sixth Day of March 1985

[SEAL]

Attest:

DONALD J. QUIGG

Attesting Officer

Acting Commissioner of Patents and Trademarks